United States Patent [19]
Garces

[11] Patent Number: 4,732,747
[45] Date of Patent: * Mar. 22, 1988

[54] MAGNESIUM SILICATE COMPOSITIONS AND PROCESS FOR MAKING

[75] Inventor: Juan M. Garces, Midland, Mich.

[73] Assignee: The Dow Chemical Company, Midland, Mich.

[*] Notice: The portion of the term of this patent subsequent to Dec. 25, 2001 has been disclaimed.

[21] Appl. No.: 700,774

[22] Filed: Feb. 12, 1985

Related U.S. Application Data

[63] Continuation-in-part of Ser. No. 484,112, Apr. 11, 1983, Pat. No. 4,499,320, which is a continuation-in-part of Ser. No. 327,870, Dec. 7, 1981, abandoned.

[51] Int. Cl.$^4$ .................. C01B 33/28; C01B 33/24
[52] U.S. Cl. ..................... 423/328; 423/331; 502/77; 502/251
[58] Field of Search ............ 423/328 T, 331, 332; 502/251, 77

[56] References Cited

U.S. PATENT DOCUMENTS

| | | | |
|---|---|---|---|
| 3,001,853 | 9/1961 | Hemstock | 423/328 |
| 3,272,594 | 9/1966 | Uyeda | 423/331 |
| 3,640,681 | 2/1972 | Pickert | 423/328 |
| 3,679,369 | 7/1972 | Miale | 423/326 |
| 3,686,341 | 8/1972 | Eberly, Jr. | 502/521 |
| 3,702,886 | 11/1972 | Argaurer | 423/328 |
| 3,761,396 | 9/1973 | Pickert | 208/111 |
| 3,887,454 | 6/1975 | Hickson | 502/251 |
| 3,892,655 | 7/1975 | Hickson | 502/251 |
| 3,893,910 | 7/1975 | Robson | 208/138 |
| 3,941,871 | 3/1976 | Dwyer et al. | 423/331 |
| 4,034,053 | 7/1977 | Kaeding et al. | 585/471 |
| 4,049,573 | 9/1977 | Kaeding | 252/432 |
| 4,049,780 | 9/1977 | Neumand | 423/332 |
| 4,061,724 | 12/1977 | Grose | 423/335 |
| 4,086,287 | 4/1978 | Kaeding et al. | 585/466 |
| 4,108,881 | 8/1978 | Rollman | 260/448 C |
| 4,148,713 | 4/1979 | Rollman | 208/111 |
| 4,229,424 | 10/1980 | Kokotailo | 423/328 |
| 257,885 | 3/1981 | Flanigen | 210/691 |

FOREIGN PATENT DOCUMENTS

| | | |
|---|---|---|
| 14545 | 3/1980 | European Pat. Off. . |
| 13630 | 7/1980 | European Pat. Off. . |
| 3622 | 8/1980 | European Pat. Off. . |
| 2830787 | 1/1980 | Fed. Rep. of Germany . |
| 2023562 | 1/1980 | United Kingdom . |
| 2024790 | 1/1980 | United Kingdom . |

OTHER PUBLICATIONS

Taramasso et al., "Molecular Sieve Borosilicates", Proceeding of the Fifth International Conference on Zeolites, pp. 40–48, Hayden & Sons Ltd. (1980).
Edmonds et al., Adv. in X Ray Anal., 22, pp. 143–150, 1978.
Edmonds, "Precision Gainier X Ray Powder Diffraction Data", NBS Spec. Publ. #567, Proceeding of Symposium on Accuracy in Powder Diffraction etc., Feb. 1980, pp. 387–389.
Nakamoto et al., Chem. Lett., 1013–1016, 1981.
Olson et al., "Chemical and Physical Properties of the ZSM 5 Substitutional Series," J. Catal., 61 390–396 (1980).
Kokotailo et al., "Pentasil Family of High Silica Crystalline Materials," Spec. Publ. Chem. Soc. 33 C. Prop. Appl. Zeolites, pp. 133–139, 1980.
U. Y-P Hong, "New Solid Electrolytes", Adv. Chem. Ser. 163, 179–184, A.C.S. 1977.
P. A. Jacobs et al., "Evidence of X Ray Amorphous Zeolites", JCS, Chem. Com. 591 (1981).
Flanigen et al., Adv. Chem. Series, vol. 101, pp. 201–209, 1971.
Breck, Zeolite Molecular Sieves, Structure Chemistry and Use, John Wiley & Sons, N.Y., N.Y., undated, pp. 294 & 298.
Barrer, Hydrothermal Chemistry of Zeolites, Academic Press, N.Y., N.Y., 1982, pp. 251–284.
Powder Diffraction File, JCPOS Swathmore Pa., 1978, pp. 275, 545, 102, 415, 310, 772, 557, 556, 712, 861, 653, 174, 895, 240, 239, 238 et al.

Primary Examiner—Gary P. Straub

[57] ABSTRACT

Novel crystalline porous magnesium silicates having catalytic activity or other useful properties ar

MAGNESIUM SILICATE COMPOSITIONS AND PROCESS FOR MAKING

CROSS-REFERENCE TO RELATED APPLICATION

This is a continuation-in-part application of Ser. No. 484,112, filed on Apr. 11, 1983, now U.S. Pat. No. 4,499,320, which is a continuation-in-part of application Ser. No. 327,870, filed on Dec. 7, 1981 now abandoned.

BACKGROUND OF THE INVENTION

The present invention relates to novel magnesium silicates and methods for their preparation. In particular, the present invention relates to novel magnesium silicates having a porous structure and catalytic properties.

Silicates are materials having as a fundamental unit a tetrahedral complex consisting of $Si^{4+}$ in tetrahedral coordination with four oxygens. Less common but also known is an octahedral complex consisting of $Si^{4+}$ in octahedral coordination with six oxygens. In some structures, the tetrahedra link to form chains or sheets. If the linking occurs in three dimensions, what is termed a framework structure results. Framework silicates may have substituted elements in place of some of the silicon atoms. A common substitution is that of aluminum for silicon forming what are known as aluminosilicates.

Zeolites are typically crystalline, hydrated aluminosilicates of Group I or Group II elements as formed in nature or synthesized. Structurally the zeolites are porous crystalline framework aluminosilicates which are based on an extending three-dimensional network work of $SiO_4$ and $AlO_4$ tetrahedra linked to each other by shared oxygens.

Molecular sieves are compositions which have the property of acting as sieves on a molecular scale. Dehydrated crystalline zeolites are important molecular sieves. Zeolites, as well as coals, oxides, glasses, intercalation compounds of graphite and alkali metals, pillared clays, and carbon absorbents are types of molecular sieves. Classification and identification of the aforementioned compositions is difficult with varied and inconsistent usage of terms found in the literature. For further information and background regarding molecular sieves and zeolites see Breck, *Zeolite Molecular Sieves*, John Wiley & Sons (1974).

Molecular sieves in general and zeolite catalysts in particular have found widespread industrial use. From a catalytic viewpoint, zeolites are molecular sieves having molecular cages with variable dimensions. Zeolite catalysts have the important properties of (1) ingress/egress control of molecules, (2) high density of "active" sites, (3) sites for occluded or deposited chemical moieties such as salts or metals, and (4) controllable potential energy fields. Zeolites are useful as catalysts in such processes as catalytic cracking, conversion of methanol to gasoline, polymerization reactions, and alkylating aromatics to mention a few. Also, molecular sieves find such utilities as acting as selective absorbents or facilitating separation of isomers.

Zeolite molecular sieves are found in nature and have been known for many years. The most siliceous natural zeolites are ferrierite, clinoptilolite and mordenite all having a $SiO_2/Al_2O_3$ ratio of about 10:1. Synthetic zeolites were first commercially produced with the introduction of zeolite A around 1954. The first synthetic zeolites had $SiO_2/Al_2O_3$ ratios in the range of 2:1 to 10:1. Later synthetic zeolites were made having molar ratios in excess of 10:1.

In 1972, U.S. Pat. No. 3,702,886 (Argauer) issued for a synthetic zeolite termed ZSM-5 and method for making same. This patent disclosed a zeolite having a $SiO_2/Al_2O_3$ molar ratio from about 5 to 100. The main claim characterized ZSM-5 by reference to a table of X-ray diffraction lines (see Table I infra) and the following composition in terms of mole ratios of oxides

$$0.9 \pm 0.2 M_{2/n}O:Al_2O_3:YSiO_2:ZH_2O$$

wherein M is at least one cation having a valence n, Y is at least 5 and Z is between 0 and 40.

TABLE I

| ZSM-5, Interplanar Spacing d(A) | | | |
|---|---|---|---|
| 11.1 ± 0.2 | 6.30 ± 0.1 | 5.01 ± 0.1 | 3.71 ± 0.05 |
| 10.0 ± 0.2 | 6.04 ± 0.1 | 4.60 ± 0.08 | 3.04 ± 0.03 |
| 7.4 ± 0.15 | 5.97 ± 0.1 | 4.25 ± 0.08 | 2.99 ± 0.02 |
| 7.1 ± 0.15 | 5.56 ± 0.1 | 3.85 ± 0.07 | 2.94 ± 0.02 |

The ZSM-5 aluminosilicate is prepared by including nitrogenous organic molecules such as tetrapropyl ammonium bromide in the reaction mixtures. For very high $SiO_2/Al_2O_3$ preparations, no aluminum need be deliberately added since it is present as an impurity in the reactants. The organic molecules are incorporated into the framework structure as it forms and these as-synthesized materials are termed "nitrogenous zeolites". Application of high temperatures will free high $SiO_2/-Al_2O_3$ materials of these organic components without altering the basic framework structure, D. M. Olson et al., "Chemical and Physical Properties of the ZSM-5 Substitutional Series", *J. Catal.*, 61, 390–396 at 391 (1980).

It is known that many properties of zeolites are primarily dependent upon the framework structure while remaining essentially invariant with composition changes such as altering the $SiO_2/Al_2O_3$ ratio. These properties include the X-ray diffraction pattern, pore size and volume, framework density and refractive index. Other properties of zeolites such as ZSM-5 will vary with composition. These properties include catalytic activity, ion-exchange capacity, and hydrophobicity (see Olson, supra, at 391).

A process for alteration of the $SiO_2/Al_2O_3$ ratio as well as zeolite composition in general was disclosed in 1973 in U.S. Pat. No. 3,761,396 (Pickert II). This patent reviews means for removing aluminum from aluminosilicates to produce more siliceous materials. This patent also reports that in some instances, aluminum in the zeolitic crystalline structure can be substituted by other metals. In a related earlier patent, U.S. Pat. No. 3,640,681 (Pickert I) which issued in 1972, the extraction of framework aluminum from large pore crystalline zeolitic molecular sieves is examined in detail. A process is claimed which utilizes acetylacetonate as an agent for aluminum removal. Also when used with a metal acetylacetonate, the metal can be substituted in the framework for the aluminum. Examples of such substitution are given which incorporate vanadium and chromium into Y zeolites. Metal acetylacetonates are preferred which utilize metals that form oxides in tri-, tetra- or pentavalent states and which are thermally stable at 600° C. However, mono- and divalent metals can also be used according to the written description which lists Mg++ as being among those metals suitable for substitution.

U.S. Pat. No. 4,049,573 (Kaeding) issued in 1977 disclosed a class of zeolites exemplified by ZSM-5, ZSM-11, ZSM-12, ZSM-35, and ZSM-38 whose members may be treated by impregnation with magnesium, boron or phosphorus compounds. These zeolites are catalysts having occluded or deposited metal moieties. These modified zeolites are useful as catalysts in hydrocarbon conversion reactions.

U.S. Pat. No. 4,061,724 (Grose) issued in 1977 for a crystalline silica composition known as "silicalite" and method for preparing same. This composition has many molecular sieve properties similar to porous crystalline aluminosilicates, but does not have ion-exchange properties which are essential to zeolitic molecular sieves. Furthermore, the silicalite does not contain $AlO_4$ tetrahedra as essential framework constituents. Silicalite has an X-ray diffraction pattern very similar to the pattern for ZSM-5.

A detailed comparison of silicalite and ZSM-5 which discloses that both silicates are members of the same structural family is presented in Olson, D. H. et al., "Chemical and Physical Properties of the ZSM-5 Substitutional Series", *J. Catal.*, 61, 390-396 (1980).

U.S. Pat. No. 4,108,881 (Rollman I) discloses an aluminosilicate zeolite termed ZSM-11. The structure of ZSM-11 has been related to that of ZSM-5 and to that of silicalite in an article by G. T. Kokotailo and W. M. Meier, "Pentasil Family of High Silica Crystalline Materials", *Spec. Publ.-Chem. Soc.*, 33 (Prop. Appl. Zeolites), 133-139 (1980). This article describes the common structural features of the above materials and proposes a generic name—pentasil—to denominate this family of structures.

U.S. Pat. No. 4,148,713 (Rollman II) discloses ZSM-5 particles having aluminum-free outer shells of $SiO_2$.

Within the group of framework silicates with tridimensional structure there is a plethora of examples which illustrate substitution of $Si^{4+}$ by metal ions other than $Al^{3+}$, as described by W. Eitel in the well-known book collection *Silicate Science*, Academic Press, 1964.

The substitution of $Si^{4+}$ by $Al^{3+}$ is common in framework silicates, but other metal ions are frequently found as substituents as well. For example, iron substitution is widespread in natural zeolites and in natural framework silicates.

Less common is the substitution of $Si^{4+}$ by divalent ions. In an article by H. Y-P Hong, "New Solid Electrolytes", *Adv. Chem. Ser.*, 163, 179-194, A.C.S. 1977, the substitution of $Si^{4+}$ by divalent ions including magnesium in framework silicates is described. H. Y-P Hong distinguishes the properties of the resulting silicates in terms of the specific cations required to balance the electronic charge of the framework.

Recently publications have issued disclosing materials resembling zeolites in crystalline structure, but not being aluminosilicates. The framework atoms of these typically pentasil structured materials contain combinations of elements other than the usual list of aluminum, silicon, oxygen, gallium or germanium.

In European Patent Office document No. 3,622 (Maas et al.) published in January of 1979, the applicant, Shell International Research, discloses a process for the preparation and separation of organic isomers using crystalline silicates which contain iron atoms within the framework structure. These silicates have a pentasil structure similar to that of ZSM-5.

In United Kingdom Patent application Nos. 2,023,562A (Taramasso I) published Jan. 3, 1980 and 2,024,790A (Taramasso II) published Jan. 16, 1980, applicant, Snamprogetti S.p.A., discloses materials giving X-ray diffraction patterns akin to ZSM-5. In the process of forming these materials, aminoalcohols, such as triethanolamine may be used. The materials formed may be used as catalysts. In addition to containing oxygen and silicon as part of the framework structure, these silicates may also include boron, beryllium, chromium, zinc, titanium, vanadium, manganese, iron, cobalt, zirconium, rhodium, silver or antimony.

In German patent document No. 2830787 (Marosi) published Jan. 23, 1980, applicant, BASF, discloses a method for the production of nitrogen-containing crystalline metal silicates with zeolite structure. This document also discusses the framework substitution of metals in place of aluminum. Boron, arsenic, antimony, vanadium, iron or chromium are given as examples of metals having a valence of three which may be substituted into the framework structure. It also states that elements such as chromium, vanadium and arsenic may be partially framework-substituted and partially deposited in the intracrystalline pores. These new materials are pentasil structured having a ZSM-5 or ZSM-8 structure in particular. A method of making this material is disclosed which utilizes hexamethylenediamine.

In United Kingdom patent document No. 2,033,358A (Morrison), published May 21, 1980, applicant, Mobil, discloses crystalline materials having ZSM-5 zeolite structures whose composition has silica to aluminum ratios ranging from about 35 to about 3000 or more. The composition of these materials may include rare earth metals, chromium, vanadium, molybdenum, indium, boron, mercury, tellurium, silver, ruthenium, platinum or palladium, however, it is unclear how these elements are related in the composition.

In European Patent Office document No. 13,630 (Rosinski), published July 23, 1980, applicant, Mobil, discloses a ZSM-12 type material which contains chromium or iron or both with the chromium and iron believed to be in positions of tetrahedral-substitution within the silica lattice.

Mobil has also disclosed in European Patent Office document No. 14,545 (Chu et al.), published Jan. 24, 1980, that the ZSM-5 class of zeolite catalysts are shape selective and that this shape selectivity can be enhanced by impregnation with magnesium or phosphorus to reduce zeolite pore openings as well as by the use of very large crystals and coke selectivation. This document further discloses impregnating or ion-exchanging a zeolite with metal-containing salts such as Mg, followed by high temperature calcination at about 649° C. or higher. In the examples, a solid-state exothermic reaction of magnesium impregnated ZSM-5 is reported at 871° C. with the reaction believed to be between magnesium and ZSM-5.

U.S. Pat No. 4,229,424 (Kokotailo), discloses a crystalline zeolite product having a structure intermediate of that of ESM-5 and ZSM-11.

SUMMARY OF THE INVENTION

The present invention is a novel porous crystalline magnesium silicate. The amount of magnesium present in this silicate may vary. However, for all compositions of the present invention, it is essential that some magnesium which is not ion-exchangeable by conventional techniques be present in the silicate. Conventional techniques of ion-exchange are presented in Breck, *Zeolite Molecular Sieves*, John Wiley & Sons (1974). Other elements may be present in these novel silicates as impurities such as aluminum, germanium, gallium, etc., or chemicals may be deliberately added either to modify or improve the properties of the magnesium silicate or for other advantageous reasons, for example, to ameliorate process parameters.

Many but not all of these novel silicates have a composition which may be expressed according to the following formula in terms of the molar ratios of oxides on a dry basis:

$$(M_{2/n}O)_p(MgO)_x(R_2O_3)_y(SiO_2)_z$$

wherein M is at least one ion-exchangeable cation having a valence of n; R is at least one element (with valence 3+) which is not ion-exchangeable by conventional means; $x/z>0$; $y/z>0$; $p/n>y$; and p, x, z are positive numbers and y is a positive number or zero. By dry basis is meant material which has been heated in air at about 500° C. for a period of one hour or more. The invention is not limited to such dried material or said oxide forms, rather its composition may be presented in terms of oxides and on a dry basis (as in the above formula) in order to provide a means for identifying some of the novel compositions. Furthermore, compositions of the present invention may also incorporate one or more elements which are not ion-exchangeable and have a valence other than 3+. These additional elements, if present, may be substituted for silicon or located as members of the framework lattice structure. In the above-mentioned formula, which accounts for some but not all compositions of the invention, element R need not be present. Other formulas may be written by those skilled in the art to identify particular subsets or embodiments of the present invention which comprises porous crystalline magnesium silicates.

Preferred novel silicates have a composition which may be expressed according to the following formula in terms of molar ratios of oxides on a dry basis:

$$(Na_2O)_p(MgO)_x(SiO_2)_z$$

wherein $x/z>0$; $x<z$ and p, x and z are positive numbers.

Magnesium silicates of the present invention have useful properties including catalytic activity. These novel compositions may be advantageously employed in known processes which presently use zeolites or compositions having zeolitic or molecular sieve properties.

Compositions of the present invention may be advantageously incorporated with binders or other materials which are well-known in the art. They may also be modified with one or more elements or compounds by deposition, occlusion, ion-exchange or other techniques known to those skilled in the art to enhance, supplement or alter the properties or usefulness of the composition. See, e.g., Breck, *Zeolite Molecular Sieves*, John Wiley & Sons (1974).

The magnesium silicates of the present invention are prepared by hydrothermal methods from a variety of silicate and magnesium sources leading to products of this invention, all of which incorporate magnesium into the structure of the resulting crystalline silicate.

DETAILED DESCRIPTION OF THE INVENTION

Figure 1:
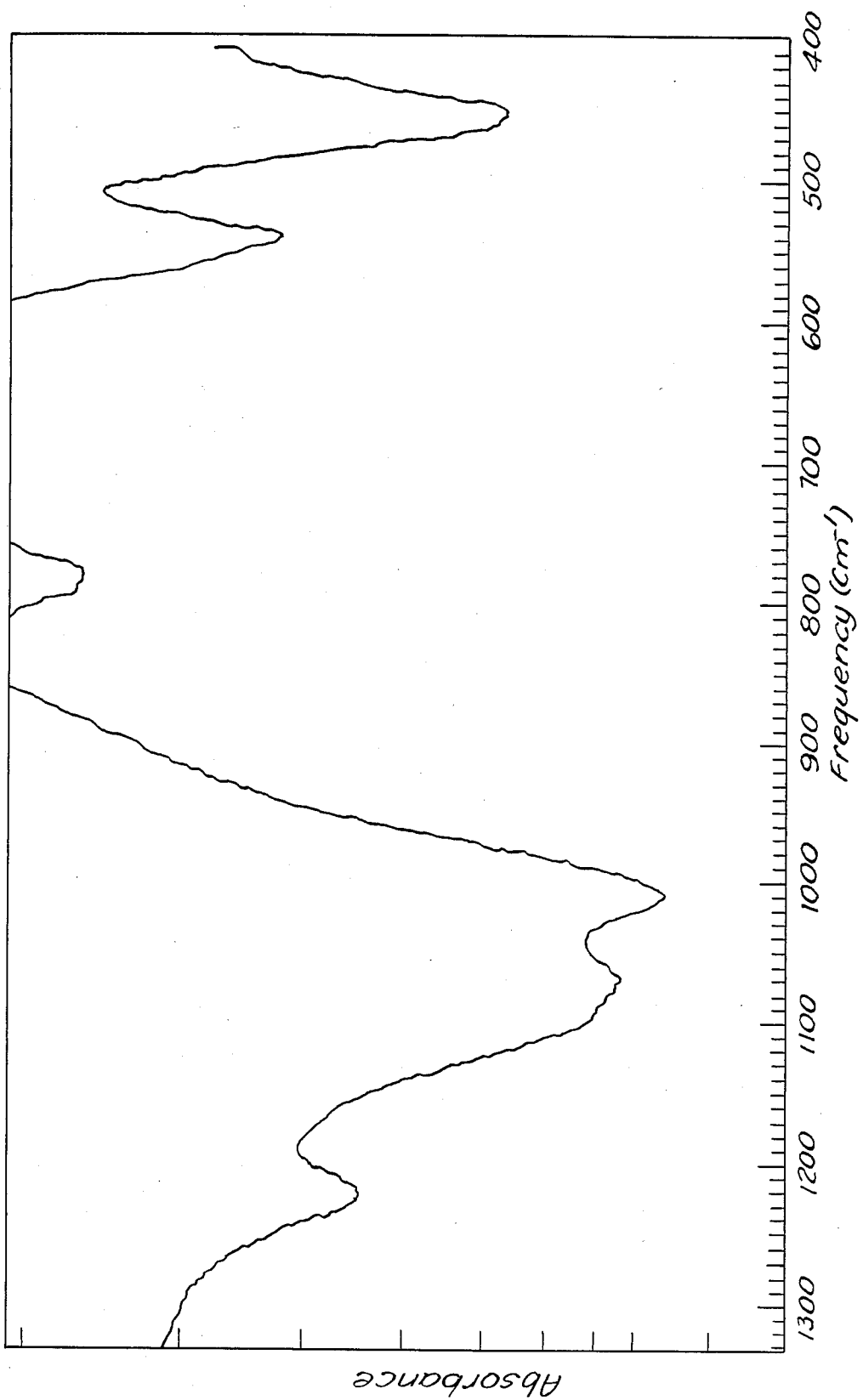

As mentioned above, the novel compositions presented have properties akin to aluminosilicate zeolites and other silicates. These properties result from the particular crystalline structure and composition of these silicates. A major problem plaguing past and current research concerning porous silicates is how to properly characterize newly synthesized materials. In "Zeolite Molecular Sieves", pages 22–26, Breck discusses at length some of the vagaries of the nomenclature employed as well as problems associated with proper characterization. Clearly the proper characterization of a previously unknown material requires structural, compositional and physicochemical information. In the past the primary criteria for characterization, particularly in the patent literature, has been (1) one or more powder X-ray diffraction patterns given to define the structure and (2) molar ratios of metal and organic oxides to define the composition. Sometimes in addition to the above, physicochemical properties such as the refractive index or absorption capacities for particular compounds or a ratio of cracking rate constants for two hydrocarbons are employed.

As progress continues in synthesizing new porous silicates with the concurrent realization that subtle changes in a material's composition and/or structure can produce significant differences in usefulness, it becomes clear that prior attempts at characterizing new materials are often inadequate. This frequent inability to adequately define or characterize newly synthesized materials properly, reflects the present skill of the art. Just as welding is often said to be more of an art than a science so too is the making of zeolites and zeolite-like materials. For example, it is known that often structural changes occur in some known zeolites merely by changing the order in which precursor materials are added or by altering stirring conditions such as the rate of stirring, the length of the mixing time or at which point in time in the process stirring commences and ends. Also with the discovery of new materials having various elements purportedly located as part of the framework structure, it becomes desirable to be able to relate composition to structure. A primary question concerning a new porous silicate containing an element Z, is the location of that element Z. Is it part of the lattice (framework structure) or is it occluded or deposited within a pore formed by the framework or is it electronically connected like those moieties which are ion-exchangeable? Merely giving a relationship between molar ratios of metal and/or organic oxides does not provide this important information and unfortunately there is no easy single means of analysis which will suffice.

The skilled artisan has difficulty in designating the location of element Z and such designations are usually made with much faith and inconclusive proof. The location of a given element in a new composition is complicated by the presence of more than one phase in the end product of many zeolite syntheses. In some instances, what appears to be a single crystalline phase is actually a mixture of closely related structures as is the case with synthetic erionite-offretite mixtures. In addition to the crystalline phases detected by X-ray diffraction in the end product, one finds amorphous material mixed with the crystalline zeolites.

Statements about the location of a given element in the crystalline phases should be based on characterization of the crystalline fraction of the products of synthesis.

From a practical point of view, the mixtures of crystalline phases and amorphous materials offer specific advantages to the user in specific applications. For this reason it is not essential to work with purified crystals in many applications. In fact, zeolites are even diluted with binders and modifiers for certain applications.

The end products of the synthesis of this invention are known to contain mainly crystalline material but they also contain amorphous silicates of magnesium. It is believed that essentially some magnesium is a part of the crystalline silicate structure. This essential portion of magnesium may be thought of as being a part of the structure in the same sense that silicon or oxygen is a part of the structure.

The term crystalline when used in this document refers to materials which are recognized by those skilled in the art as having a highly ordered structure. Three dimensional periodicity is characteristic of a highly ordered structure. The skilled artisan recognizes that evidence of such periodicity may be presented by catalytic reactivity, infrared spectroscopy or other means of analysis as well as by the commonplace X-ray diffraction analysis. Silicates of the present invention are "crystalline" as that term is characterized above even if said silicates appear amorphous to X-ray diffraction analysis if a skilled artisan recognizes a highly ordered structure by other evidence. A recent article by P. A. Jacobs et al., "Evidence of X-ray Amorphous Zeolites", *J.C.S. Chem. Comm.*, 591, 1981, is hereby incorporated by reference in its entirety in this document.

By the term "porous" are meant those silicates having a framework structure containing cavities capable of allowing the entrance or absorbence of molecules such as water, nitrogen or toluene, etc.

Due to the differences in ionic radii of $Si^{IV}$ (0.41 Angstroms (Å)) and $Al^{III}$ (0.50 Å) replacement of Si by Al in $TO_4$ sites will cause a unit cell volume expansion in most zeolites. The degree of unit cell volume expansion will depend on the amount of Al substitution for Si in the $TO_4$ sites. If the substitution is low, as in some ZSM-5 and silicalite zeolites, high resolution, calibrated X-ray diffraction techniques must be utilized to detect the expansion.

Similarly, in the present invention, it is believed that nonion-exchangeable Mg is contained in the zeolite lattice. Replacement of $Si^{IV}$ (0.41 Å) by $Mg^{II}$ (0.65 Å) in $TO_4$ sites will also cause a unit cell expansion. Once again, the amount of Mg substitution for Si, will influence the degree of cell volume expansion.

Evidencing element location in a framework lattice structure by determining cell volume expansion (contraction) has been done by others skilled in making silicates. See, e.g., M. Taramasso, G. Perego and B. Notari, "Molecular Sieve Borosilicates", *Proceedings of the Fifth International Conference on Zeolites*, 40-48 at 44 (Heyden & Sons Ltd.) (1980).

High resolution X-ray powder diffraction data were obtained from Huber-Guinier powder diffraction cameras equipped with Ge and quartz monochromators for providing $CuK_{\alpha 1}$ and $FeK_{\alpha 1}$ radiation, respectively. The films were calibrated, with well-known internal standards such as NBS Si (NBS Circular 539 Vol. 9, p. 3) or $AS_2O_3$, scanned with a densitometer and the resulting data profile fit by techniques described in: J. W. Edmonds and W. W. Henslee, *Adv. in X-ray Anal.*, 22, 143 (1978) and J. W. Edmonds, "Precision Guinier X-ray Powder Diffraction Data", NBS Special Publication 567, *Proceedings of Symposium on Accuracy in Powder Diffraction Held at NBS, Gaithersburg, Md.*, June 11-15, 1979 (Issued February 1980) (the papers are hereby incorporated by reference). The calibrated data were least-squares refined and fitted to obtain accurate cell dimensions and volumes.

Using data from the method described above and using single crystal X-ray crystallographic data from the literature, the cell volume for the present invention where $Mg^{II}$ is believed to replace $Si^{IV}$, can be compared to the cell volume of silicalite which has $Si^{IV}$ in all the $TO_4$ sites. Typical data are shown in Table II, for either anhydrous zeolites or calcined zeolites. (Minimum calcination of 500° C. for 1 hour.)

TABLE II

| Compound | Cell Volumes Volume (Å³) | Reference |
|---|---|---|
| Silicalite | 5306 | 1 |
| Silicalite | 5305 | 2 |
| Magnesium Silicate | 5347 | 2 |
| Magnesium Silicate | 5349 | 2 |

[1] Cell volumes were obtained from the lattice parameters given in an article by E. M. Flanigen, J. M. Bennett, R. W. Grose, J. P. Cohen, R. L. Patton, R. M. Kirchner and J. V. Smith, Nature, 271, 512 (1978).
[2] Cell volumes were calculated using the National Bureau of Standards - Geological Survey Lattice Parameter Refinement Program written by Dan Appleman (available through NTIS) on XRD data obtained on samples made either according to a process of the invention or according to the silicalite patent.

The above values are typical examples of cell volumes. The difference between these volumes show a cell volume expansion. The exact amount of expansion will be composition dependent. The compounds of the present invention will exhibit unit cell volume expansion when compared to silicalite, but expansion is not limited to that derived from the data shown in Table II. It is believed that the above-mentioned unit cell expansion evidences the placement of magnesium as a part of the lattice framework structure. It is believed, without wishing to be bound by that belief, that altering the $SiO_2/MgO$ ratio varies the pore size and volume, framework density and refractive index of the resulting magnesium silicates. If small ranges of the $SiO_2/MgO$ ratios are utilized, the ability to detect volume, pore size and density differences will be dependent on the resolution capabilities of the analytical technique used.

Samples of compositions of the present invention whose crystallite size is appropriate to produce a distinct X-ray powder diffraction trace, have a pattern which includes at least the interplanar d spacings listed in Table III.

TABLE III

| Magnesium silicate, interplanar spacings d(Å) |
|---|
| 11.2 ± 0.2 |
| 10.1 ± 0.2 |
| 10.0 ± 0.2 |
| 9.8 ± 0.2 |
| 6.0 ± 0.2 |
| 5.8 ± 0.2 |
| 5.6 ± 0.2 |
| 4.26 ± 0.1 |
| 3.85 ± 0.05 |
| 3.81 ± 0.05 |
| 3.74 ± 0.03 |
| 3.72 ± 0.03 |
| 3.64 ± 0.03 |

The range cited is due to unit cell volume expansion with decreasing $SiO_2/MgO$ ratio. Magnesium silicates with low Mg content in the $TO_4$ sites will be near the low d spacing limit and those with high Mg content in $TO_4$ sites will be near the high d spacing limit.

This invention is further characterized by a minimum of two reflections at 10.1±0.3 Å and a minimum of four reflections between 3.69 and 3.90 Å.

These values were obtained by Huber-Guinier techniques (preferred method) mentioned previously or by a Philips Electronics X-ray powder diffraction unit equipped with: scintillation-counter detector, graphite monochromator, and a strip chart recorder. The recorded reflections were identified by their two theta locations, after these locations were calibrated with an internal standard. The standard used was either NBS Si (NBS Circular 539, Vol. 9, p. 3) or $As_2O_3$. The magnesium silicate diffraction peaks at approximately 10.0 and 3.81 Å can often be obscured in poorly crystalline samples or in low-resolution X-ray diffraction data.

X-ray analyses of magnesium silicates of the present invention reveal distinct differences in the diffraction patterns as a result of specific treatments given to these magnesium silicates. Intensity changes are observed and lines may appear, disappear or merge depending on the exact calcination procedure utilized. Ion-exchange of these silicates may also cause changes in certain cases. Several authors have made similar observations on related materials like zeolite ZSM-5. See H. Nakamoto and H. Tarahashi, *Chem. Lett.* 1013–1016 (1981). Regardless of the causes of the above-mentioned changes, they are expected by those people skilled in the art of analyzing porous crystalline silicates.

The magnesium silicates of this invention are characterized also by infrared analysis. The use of infrared analysis is recognized as a standard method in the characterization of inorganic and organic materials and has been used in the study of both natural and synthetic zeolites. See for example, E. M. Flanigen et al., *Adv. Chem. Series*, Vol. 101, p. 201-229, 1971. See also P. A. Jacobs, supra. For examples from the patent literature pertaining to the use of infrared analysis in zeolite characterization, see U.S. Pat. No. 4,257,885 to R. W. Grose and E. M. Flanigen and references included therein.

Figure 2:
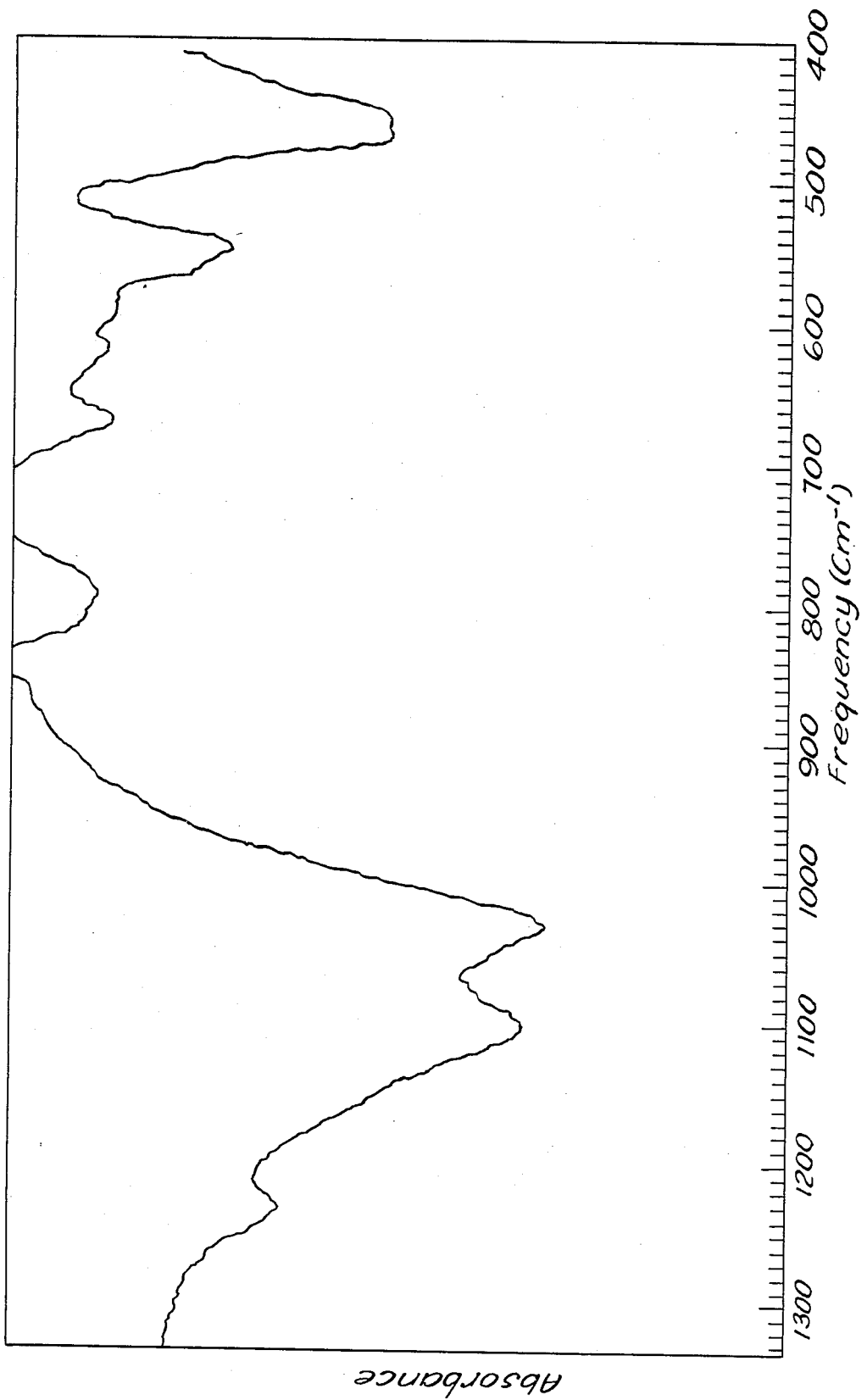
Figure 3:
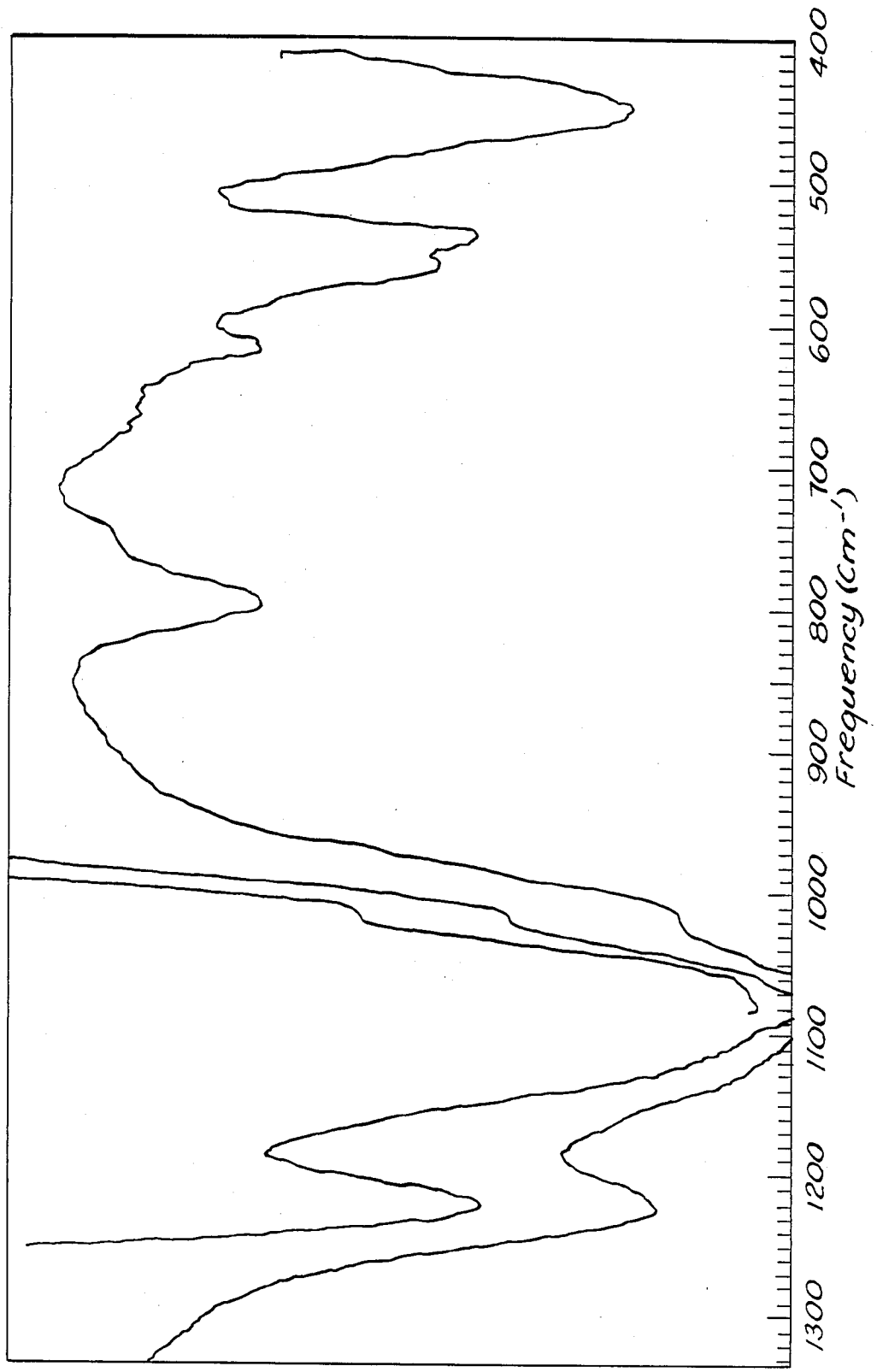

Magnesium silicates of the present invention exhibit unique features in the 1300–400 $cm^{-1}$ region. Many compositions of this invention exhibit at least two distinct bands in the 1200–980 $cm^{-1}$ region as shown in FIGS. 1, 2 and 3. Preferred compositions of the present invention exhibit these two distinct bands and also characteristic infrared bands at 1225±10 $cm^{-1}$, 800±20 $cm^{-1}$, 620±10 $cm^{-1}$, 550±20 $cm^{-1}$ and 450±20 $cm^{-1}$ as shown in FIGS. 1, 2 and 3.

Without wishing to be bound by any theory, it should be recognized that bands located between 1200–980 $cm^{-1}$ may be due to asymmetric stretch of $TO_4$ units in zeolites and silicates, see, e.g., Flanigen et al. "Molecular Sieve Zeolites-1," *Adv. Chem. Series*, 101, 201 A.C.S. (1971). It is believed without being bound by that belief that the band found nearest to 980 $cm^{-1}$ in the present invention is due to silanol groups of the form —Si(OH)$_3$, >Si(OH)$_2$, →SiOH, or to their corresponding silicate forms.

Differential thermal analysis (DTA) is one of the thermal methods used in the literature as an aid in zeolite characterization. See D. W. Breck, *Zeolites Molecular Sieves*, John Wiley, 1974. See also European Patent Office Document No. 14,545 (Chu et al.), Jan. 24, 1980.

Compositions of the present invention may be analyzed by DTA methods. When using a Dupont ® 990 thermal analysis unit equipped with a 1200° C. furnace, a 10 mg sample is tested against alumina as a reference material (both contained in platinum crucibles). The heating rate for the system is 20° C. per minute in air with an air flow rate of 50 cc per minute. Under these conditions, one observes a distinct exotherm therm at 870°±30° C. X-ray diffraction (XRD) analysis of the sample both before and after the exotherm yields at least the interplanar d spacings listed in Table III, supra.

The compositions of this invention have ion-exchange properties. The ion-exchange capacity of traditional zeolites is associated with their aluminum content. The ion-exchange properties of the magnesium silicate of this invention are not necessarily dependent upon any one of its particular components. Indeed it is believed, without wishing to be bound to this belief, that the ion-exchange capacity of the present invention is due to a combination of factors. Among them are: the magnesium content, the trivalent metal ion content and also to the presence of internal silanol moieties within the silicate framework which under appropriate conditions can participate in the ion-exchange process.

Even though a relationship among the composition and the ion-exchange capacity of these solids is recognized, the present invention is not restricted by the traditional "linear relationship" between composition and ion-exchange capacity, characteristic of traditional zeolites.

The exchangeable cations in zeolite compositions often play a critical role in their synthesis by hydrothermal methods. In certain cases, a particular cation is required to obtain a given zeolite, for example, sodium is said to be required to produce zeolite X from aluminosilicate gels. Apparently the cation plays a template role in the formation of certain structures and/or acts as a crystallization promoter. The magnesium silicates of this invention do not appear to require a particular alkali metal cation for their formation. Crystalline compositions of the present invention are obtained from magnesium silicate gels in the presence of several alkaline metal salts including sodium or potassium salts. The presence of sodium or potassium ions during and/or after the synthesis may affect certain properties of the final product in applications which are susceptible to drastic changes by subtle differences such as catalysis and adsorption. Salts other than sodium and potassium may have similar effects.

In the synthesis of traditional zeolites the source of silica may be a critical factor in the preparation of certain zeolites. In the case of the present invention, the source of silica appears to have an effect in the morphology of the crystalline product. There are many examples in the literature relating morphology to a variety of useful properties of porous crystalline silicates like catalytic applications, ion-exchange, adsorption, etc.

Typically, the novel material is made by hydrothermal methods using one of many sources of silicon such as one of the commercially available soluble silicates or water glass solutions, amorphous silica, colloidal silica, silica gels, fumed silica or an organosilicate like $(EtO)_4Si$. Advantageously employed are two commercially available sources: a colloidal silica sold by the du Pont de Nemours Company under the trademark Ludox SM ® and a sodium silicate sold by the Philadelphia Quartz Company under the trademark Philadelphia Quartz Sodium Silicate N ®.

The source of magnesium usually is one of its water-soluble salts, magnesium chloride, acetate, sulfate, nitrate, etc., or a complex ion like $Mg(NH_3)_6^{2+}$, $Mg(EDTA)^{2-}$, etc., or a slightly soluble compound like $Mg(OH)_2$, $MgF_2$, etc. A magnesium chloride salt is a preferred source of magnesium.

Besides these components the reaction mixture will contain a solvent such as water, along with alkali metal ion salts such as, chlorides, sulfates or hydroxides of sodium, potassium, rubidium or cesium. The solvent may be added separately to the reaction mixture or may already be present with one of the reactants such as the silica source. Water is the preferred solvent.

A material which is believed, without wishing to be bound by that belief, to act as a crystallization promoter and is hereinafter termed a "crystallization promoter" is utilized in the process of making the porous crystalline magnesium silicate of the present invention. Typically, this crystallization promoter is (or is formed from) an organic nitrogen compound such as quaternary ammonium ion salts, or hexamethylene diamine, but may also be other compounds such as seed crystals typically of compositions similar to those crystals sought from the process. In particular, tetrapropyl ammonium ion salts are often used with tetrapropyl ammonium bromide and tetrapropyl ammonium hydroxide being preferred.

In a typical method of making these novel magnesium silicates, a magnesium source, a crystallization promoter, an alkali metal ion salt and a solvent are combined. The pH of this combination of chemicals is usually adjusted and the combination is further combined with a mixture of a silica source and a solvent to give a reaction mixture typically having a pH of about 11. The pH may advantageously be adjusted either above or below a pH of 11 to modify certain crystallization or process parameters such as the solubility of magnesium in the mixture, formation of precipitates, rates of crystallization, etc. The pH is adjusted as desired using acids or bases such as $H_2SO_4$ or NaOH and may be adjusted before, after and/or during the mixing step of the reactants.

The reaction mixture is vigorously mixed at room temperature for a sufficient time to produce an apparently homogeneous gel. Typically the rate of mixing is sufficiently vigorous to produce a satisfactory slurry or gel within one minute.

The mixture resulting from the above procedure is allowed to crystallize into compositions of the present invention. Preferably, crystallization takes place at temperatures above room temperature to increase the rate of crystal growth. Usually about 150° C. is used with autogeneous pressure. Higher or lower temperatures may be advantageously employed depending upon the process or product parameters desired, e.g., larger crystals are generally formed with lower temperatures and the rate of crystallization increases with higher temperatures. When quaternary ammonium ion salts are used as crystallization promoters, temperatures above 200° C. are avoided to prevent their decomposition.

Crystallization is allowed to proceed until crystals of the compositions of the present invention are formed. This may be determined by analysis of reaction mixture samples at intervals. The crystallization time will vary depending upon the reactants or the particular process parameters chosen. Crystallization times of one to five days are not uncommon.

During the crystallization step, stirring may be advantageously employed to facilitate product formation.

The rate and type of stirring may affect crystallization parameters such as the rate of crystallization, uniformity of the product and crystal size. The effect of this parameter and optimum adjustment is dependent upon other parameters and is believed to be within the skill of the art to determine without undue experimentation.

Following crystallization it is often desirable to filter the crystallized mixture using a water wash to remove the mother liquor and then to heat the crystals to about 110° C. to remove water and thereby produce a convenient free-flowing powder.

The compositions as made by the above procedure may contain organic moieties which, if desired, may be removed by known methods such as calcination in an oxygen-containing atmosphere at a temperature sufficient to decompose the organic moieties. Calcination at about 500° C.-600° C. for approximately an hour is sufficient to remove commonly present organic moieties.

As mentioned before, the magnesium silicates of the invention may be beneficially modified by techniques well-known in the art which treat said silicates with acids, salts or other ions or molecules. Acid treatment is especially valued to produce a stable, catalytically active form of porous crystalline magnesium silicate.

As mentioned before, certain compositions of the invention may be expressed according to a formula in terms of the molar ratios of oxides on a dry basis, viz.,

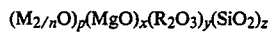

$$(M_{2/n}O)_p(MgO)_x(R_2O_3)_y(SiO_2)_z$$

wherein M is at least one ion-exchangeable cation having a valence of n; R is at least one element with valence 3+ which is not ion-exchangeable by conventional means; $x/z \geq 0$; $y/z > 0$; $p/n \geq y$; and p, x, z are positive numbers and y is a positive number or zero. The statement $x/z > 0$ is essential to all compositions of the present invention since it defines a magnesium silicate. All compositions of the present invention must contain magnesium.

The statement $y/z \geq 0$ indicates that this is a nonessential term. Typical nonion-exchangeable elements which may advantageously be present include by way of example, aluminum, iron, chromium, boron and gallium.

Also the above-mentioned formula could be modified to include other elements optionally present which are not ion-exchangeable by conventional means having a valence other than 3+ such as 2+ or 4+. Germanium is an example of such an element.

Preferred embodiments of the present invention expressed in terms of the above formula are those wherein p is from about 0.1 to about 4, most preferably from about 0.1 to about 2.0; x is from about 0.01 to about 2, most preferably from about 0.01 to about 0.5; y is from about 0 to about 3 and z is from about 90 to about 96. It is especially preferred that the term y of the above formula be from 0 to about 1.0.

Typically, the ion-exchangeable cations M (of both the magnesium silicates represented by the above formula and similar magnesium silicates of the present invention) are alkali metals, hydrogen, group VIII metals or rare earth elements, or ammonium ions, but may be any element or moiety capable of exchange into the magnesium silicates of the present invention. Preferred are hydrogen, the alkali metals and the rare earth elements. Methods of ion-exchange are well-known in the art, e.g., hydrogen may be exchanged into a silicate by simply treating with acid.

The above description and following examples are given to illustrate the invention and methods of making the invention, but these examples should not be taken as limiting the scope of the invention to the particular embodiments or parameters demonstrated since obvious modifications of these teachings will be apparent to those skilled in the art.

EXAMPLE 1

A solution A is made by combining 106 g of commercially available Philadelphia Quartz Sodium Silicate N ® type (trademark of Philadelphia Quartz Company) (8.90 weight percent $Na_2O$, 28.7 weight percent $SiO_2$) with 132 g of $H_2O$. A second solution B is made by combining 180 g of $H_2O$, 40 g of NaCl, 26 g of $(C_3H_7)_4NRr$, 10.2 g $MgCl_2$ $6H_2O$ and 8 g of concentrated $H_2SO_4$ (96 weight percent) to form a clear solution.

Solution A is transferred to a Waring ® blender and the blender is started at the "high" setting. Solution B is added at once and the mixture is stirred vigorously for 1 minute. The resulting slurry is then placed inside a stainless steel autoclave, heated to about 150° C. under autogenous pressure and stirred. After 24 hours, the autoclave is cooled to room temperature and the solid product is isolated by filtration. The filter cake is washed several times with much water and then air dried at about 110° C. into a free flowing powder. X-ray powder diffraction (XRD) analysis of the powder gives a pattern similar to that reported for silicalite and ZSM-5.

EXAMPLE 2

A product made according to the procedure of Example 1 which is calcined overnight in air at about 500° C. to remove trapped organic matter produces changes in the relative intensities observed by XRD analysis.

Surface area measurements on a calcined solid, made according to the above procedure, by the single point BET method gives a measurement of 378 $m^2/g$.

Analysis of a product made according to the procedure in Example 1 by infrared spectroscopy using a Perkin-Elmer ® Model 337 double-beam instrument produces a characteristic spectrum with two distinct bands in the 1200-980 $cm^{-1}$ region.

Differential thermal analysis of a solid silicate (as made according to the procedure in Example 1) using a DuPont ® 990 thermal analysis unit equipped with a 1200° C. furnace reveals a characteristic exotherm at about 860° C. The sample is heated at a rate of about 20° C./minute in a platinum crucible in an air atmosphere with an air flow rate of about 50 cc/minute. The product is recovered after heating to about 950° C. and is analyzed by XRD and is found to contain all the lines listed in Table III.

EXAMPLE 3

The procedure of Example 1 is repeated but with a reaction temperature of 125° C. rather than 150° C. The solid dried at 110° C. is calcined at about 500° C. for 18 hours. Chemical analysis of the solid is done by neutron activation analysis and revealed on a molar ratio basis referred to $MgO:SiO_2$ (11.0), MgO (1.0), $Na_2O$ (0.38) and $Al_2O_3$ (0.015). The XRD analysis of the magnesium silicate product is consistent with the diffraction lines listed in Table II.

EXAMPLE 4

A reaction mixture is prepared as follows: (a) 100 g of commercially available Ludox SM ® (trademark of DuPont) colloidal silica (30 weight percent $SiO_2$, 0.56 weight percent $Na_2O$) are mixed with 8.0 g of NaOH solution (50 weight percent NaOH) and 100 g of $H_2O$; (b) 26 g of $(C_3H_7)_4NBr$ are dissolved in 110 g of $H_2O$; (c) 10.2 g of $MgCl_2$ $6H_2O$ are dissolved in 100 g of $H_2O$.

The mixtures of (a) and (b) are mixed in a high torque blender for a few seconds and then solution (c) is added maintaining the mixing for about 1 minute to produce an apparently homogeneous mixture. The pH of the mixture is adjusted to about 11 by addition of NaOH (50 weight percent NaOH). The pH adjusted mixture is then transferred to a stainless steel autoclave and stirred at 150° C. for 30 hrs. under autogenous pressure. The product is recovered by filtration and rinsed with copious amounts of water. The lines observed by X-ray powder diffraction analysis of the solid match those values listed in Table III.

EXAMPLE 5

A porous crystalline magnesium silicate that is prepared according to the process of the invention is calcined overnight to remove organic moieties. This calcined material is then slurried with hot 1N $NH_4NO_3$ overnight. The material recovered by filtering this slurry is dried for several hours at about 110° C. Then one part of this magnesium silicate is mixed with one-half part kaolin clay and enough water to form a moist cake. The cake is dried and then calcined at about 500° C. in air for about 5 hours. This material is then crushed into 6-12 mesh aggregates.

About 9 g of the crushed aggregate is placed into the center portion of a ½"×30" 316 stainless steel reactor tube with 8-12 mesh silica on both sides acting as a support and aid to the uniform heating of the catalyst. A ⅛" thermowell inside the reactor is equipped with a thermocouple for measuring reactor temperatures. The reactor is placed inside an electric furnace and heated to about 370° C. A hydrogen gas feed is begun and the pressure increased to about 100 psig and then toluene is fed to the reactor. When toluene is detected downstream from the reactor, the ethylene feed is started.

The toluene is pumped into the reactor at a rate of about 121 g per hour, hydrogen gas is added at a rate of about 240 cc per minute as measured at ambient pressure and temperature, and ethylene is added at a rate of about 75 cc per minute as measured at about 21° C. and about 760 mm Hg pressure. The reactor is operated at about 100 psig with a negligible pressure drop across the catalyst bed.

About 3½ hours after the ethylene feed stream is turned on, a sample of the reactor effluent is taken and analyzed by conventional gas chromatographic methods. The results are given in Table IV below.

TABLE IV

| Reactor Effluent Analysis | |
|---|---|
| | Mole Percentage in Liquid Effluent |
| Benzene | 0.03 |
| Toluene | 88.15 |
| EBX* | 0.126 |
| para-Ethyltoluene | 7.83 |
| ortho-Ethyltoluene | — |
| meta-Ethyltoluene | 3.55 |

TABLE IV-continued

Reactor Effluent Analysis

| | Mole Percentage in Liquid Effluent |
|---|---|
| DEB** | 0.15 |

*Ethylbenzene and xylenes.
**Diethylbenzene.

The molar feed ratios for the above process are approximately 7 to 1 to 3 for toluene to ethylene to hydrogen. The above analysis gives approximately an 80.1 percent conversion rate to ethyltoluene for ethylene based upon a maximum theoretical conversion calculated by dividing the mole per hour feed rate for ethylene by that for toluene.

EXAMPLE 6

A reaction mixture is prepared as follows: (a) 530 g of Philadelphia Quartz N ® type sodium silicate are mixed with 660 g $H_2O$, and (b) 200 g of NaCl, 50.8 g $MgCl_2.6H_2O$, 130 g of $(C_3H_7)_4NBr$, 40 g $H_2SO_4$ solution (96 weight percent $H_2SO_4$) and 900 g of $H_2O$ are mixed.

Solution (a) is transferred to a high torque blender and solution (b) is added to it maintaining continuous stirring. When the addition is finished, the slurry is stirred for about 1 minute. The homogeneous slurry is transferred to a stainless steel autoclave and stirred at about 125° C. under autogenous pressure for about 26 hours. The resulting product is separated by filtration and dried at about 110° C. overnight.

Analysis of the product by X-ray powder diffraction shows that the magnesium silicate contains the lines listed in Table III. Surface area analysis of the calcined product by the one point BET method gave about 395 $m^2/g$.

A portion of the product dried at 110° C. is extracted with EDTA, calcined at 500° C. and separate samples of this portion are ion-exchanged with 0.01 M NaOH and 0.01 M KOH solutions, respectively. Analysis of the exchanged products by neutron activation analysis gives the following results on a molar basis referred to MgO.

TABLE V

| Solid | $SiO_2$ | MgO | $Na_2O$ | $K_2O$ | $Al_2O_3$ |
|---|---|---|---|---|---|
| NaOH Xged. | 8.9 | 1.0 | 0.040 | 0.005 | 0.01 |
| KOH Xged. | 8.3 | 1.0 | 0.005 | 0.040 | 0.01 |

Infrared analysis of the solid either as made, or after calcination, or after NaOH or KOH ion-exchange reveals two characteristic bands in the 1200–980.0 $cm^{-1}$ region. From the data shown in Table V, it is seen that the ion-exchange capacity is greater than that attributable to the presence of aluminum.

EXAMPLE 7

This synthesis is carried out according to the following procedure: (a) 600 g of Ludox SM ® colloidal silica (30 weight percent $SiO_2$, 0.56 weight percent $Na_2O$), 63.5 g of KOH pellets and 650 g of $H_2O$ are mixed; (b) 305 g of KCl, 156 g of $(C_3H_7)_4NBr$ and 660 g of $H_2O$ are mixed; and (c) 61 g of $MgCl_2.6H_2O$ are dissolved in 600 g of $H_2O$.

Solution (b) is added to solution (a) in a high torque blender followed by solution (c). The final mixture is stirred for about 1 minute into a homogeneous slurry. The slurry is transferred to a stainless steel autoclave and stirred at about 175° C. for approximately 72 hours. The product is recovered by filtration, washed with $H_2O$ and dried at about 110° C. overnight in air.

XRD analysis of the solid indicates that the material is crystalline corresponding to the features listed in Table III. Infrared analysis of the solid shows two characteristic bands in the 1200–980 $cm^{-1}$ region.

A portion of the solid is extracted with EDTA, etc., in the manner indicated in Example 6 and analyzed by neutron activation analysis. The following results on a molar basis referred to MgO correspond to the NaOH and KOH exchanged samples:

TABLE VI

| Solid | $SiO_2$ | MgO | $Na_2O$ | $K_2O$ | $Al_2O_3$ |
|---|---|---|---|---|---|
| NaOH Xged. | 8.5 | 1.0 | 0.040 | 0.02 | 0.008 |
| KOH Xged. | 8.0 | 1.0 | 0.002 | 0.05 | 0.009 |

Differential thermal analysis, according to the procedure of Example 2, of the solid as made gives a characteristic exotherm at about 880° C.

EXAMPLE 8

A solution A is made by combining 795 g of N ® type sodium silicate (trademark of the PQ Corporation) (8.90 percent $Na_2O$, 28.7 percent $SiO_2$) with 1020 g of $H_2O$. A second solution B is made by combining 300 g of NaCl, 76.2 g of $MgCl_2$ $6H_2O$, 195 g of $(C_3H_7)_4NBr$, 1230 g of $H_2O$ and 55 g of concentrated $H_2SO_4$ (96 percent) to form a clear solution.

The solutions are mixed by pumping 1815 g of solution A and 1754 g of solution B at 250 ml/min each into the mixing head of a Tekmar mixer model LD-45. The mixer is set at 90 percent of its maximum speed. A smooth slurry is obtained. This slurry (2432 g) is transferred into a Teflon lined autoclave at 125° C. under autogeneous pressure and stirred at 500 rpm. After 70 hours, the autoclave is cooled to room temperature and the solid product is isolated by filtration.

About one gram of the filter cake is reslurried in 15 ml of $H_2O$ in a test tube, and the mixture is centrifuged to separate the solids from the liquid. This operation is repeated twice discarding the clear filtrate. Two layers of solid are observed in the test tube. The two layers are separated and analyzed. The top layer is amorphous and the lower one is crystalline as shown by X-ray analysis. The crystalline layer has all the diffraction peaks listed in Table III.

Energy Dispersive Spectroscopy analysis shows Si, Na, and Mg in both layers. The amorphous one also contains Cl and higher concentrations of Na and Mg than the crystalline layer.

The remainder of the filter cake (1460 g) is used to separate the amorphous from the crystalline material following the same technique described above.

A high purity crystalline sample is made repeating the procedure 10 times. This sample is used for a variety of analyses.

Neutron activation analysis is used for the determination of concentrations of Na, Mg, Al and Si, and concentrations of C, H and N are determined by combustion. The composition is summarized in Table VII.

TABLE VII

Elemental analysis and molar ratios of purified NaMg silicate crystals

| Components | Weight Percent | Analytical Method |
|---|---|---|

TABLE VII-continued

Elemental analysis and molar ratios of purified NaMg silicate crystals

| | | |
|---|---|---|
| $SiO_2$ | 88.6 | Neutron Activation |
| MgO | 0.45 | Neutron Activation |
| $Na_2O$ | 1.22 | Neutron Activation |
| $Al_2O_3$ | 0.013 | Neutron Activation |
| C | 7.95 | Combustion |
| H | 1.86 | Combustion |
| N | 0.74 | Combustion |
| Total | 100.8 | |

| Elements | Molar Ratio |
|---|---|
| Si/Mg | 128.0 |
| Si/Al | 5500.0 |
| Na/Mg | 3.56 |
| Si/N | 27.0 |
| C/N | 12.5 |

Electron microprobe analysis of thin sections of the crystalline particles indicates that the magnesium concentration in the aggregates is not uniform, ranging from 400 ppm at the core to 3000 ppm at the surface. Aluminum is not detected within the crystalline particles. The amorphous material present in the samples which is not purified contains 13 percent magnesium as a silicate mixed with NaCl crystals.

Microscopic analysis of the purified crystalline materials shows uniform particles of 8 microns in diameter with rounded corners and almost square shape.

X-ray analysis of the purified crystals using a Gunier camera indicates that the symmetry is orthorhombic. The unit cell dimensions are: a(Å)=20.024(5), b(A)=13.380(4), c(Å)=19.903(3), β(degrees)=90. The unit cell volume V(Å³) is 5.332(2). The X-ray powder diffraction pattern of the sample experiences a variety of changes when the crystalline material is calcined to remove organic moieties. First, the reflection at about 12.05 degrees 2θ drops in intensity and splits when the solid is calcined. The doublet at around 14.8 degrees 2θ collapses into a single peak and its intensity decreases. The single peak at 24.5 degrees splits into two peaks of lower intensity. A similar change occurs at the peak at 26.1 degrees 2θ, etc. Also, there are obvious changes in intensity of the peaks between 7-10 degrees and 22-25 degrees 2θ. These phenomena are associated with a symmetry change from orthorhombic to monoclinic when the crystalline material is calcined.

BET adsorption-desorption isotherms of $N_2$ on the purified crystals after calcination in air at 500° C. show a very flat and almost hysterisis free isotherm. The BET surface area is 521.07 m²/g. The micropore volume (t-plot) is 0.191 cm³/g. The least squares surface are (t-plot) is 1.95 m²/g. Apparently, the calcined crystalline material is free of meso and macropores.

Infrared analysis of the crystalline material before and after calcination shows the presence of at least two distinct bands in the 1200-980 $cm^{-1}$ region and at least one or more additional bands at 1225±10 $cm^{-1}$, 800±20 $cm^{-1}$, 620±10 $cm^{-1}$, 550±20 $cm^{-1}$ and 450±20 $cm^{-1}$.

In addition to the obvious exotherms associated with combustion of organic moieties below 500° C., differential thermal analysis of the purified crystalline material shows an exotherm between 800° C. and 900° C. and another at 1020° C. This last exotherm (1020° C.) is associated with a collapse of the crystalline material into amorphous material and/or cristobalite, a dense silica polymorph.

A calcined sample of the purified crystals is exchanged with 0.1 N NaOH using 100 ml/g of solid equilibrating for one day at room temperature. Back exchange with 0.1 N KCl under similar conditions gives a capacity of 0.34 meq Na/g of solid.

The purified crystalline material is evaluated as an alkylation catalyst in the alkylation of toluene with ethylene and is found to be active with results comparable to those reported in Table V. These results demonstrate that separation of the amorphous and crystalline components is not essential to obtain an active catalyst.

As mentioned before, the above examples serve only to illustrate the invention and its advantages, and they should not be interpreted as limiting since further modifications of the disclosed invention will be apparent to those skilled in the art. All such modifications are deemed to be within the scope of the invention as defined in the following claims.

What is claimed is:

1. A porous crystalline magnesium silicate having a three dimensional lattice and a composition according to the following formula in terms of the molar ratios of oxide on a dry basis:

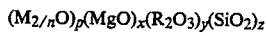

$$(M_{2/n}O)_p(MgO)_x(R_2O_3)_y(SiO_2)_z$$

wherein M is at least one ion-exchangeable cation having a valence n; R is a trivalent element or mixture thereof which is not ion-exchangeable by conventional means; x/z≧0; y/z≧0; p/n≧y; and p, x, z are positive numbers with p being from about 0.1 to about 4, x being from about 0.01 to about 2, z being from about 90 to about 96 and y being zero or a positive number from about 0 to about 3 further characterized by an X-ray diffraction trace having at least those interplanar d spacings listed in Table III of the specification and further provided that nonion-exchangeable cation and further provided that nonion-exchangeable magnesium is contained in the lattice and further characterized by infrared analysis in that said analysis exhibits at least two peaks in the 1200-980 $cm^{-1}$ region.

2. A porous crystalline magnesium silicate as defined in claim 1 wherein y is from zero to about 1.0.

3. A porous crystalline magnesium silicate as defined in claim 1 wherein M is an alkali metal cation.

4. A porous crystalline magnesium silicate as defined in claim 1 wherein M is hydrogen.

5. A porous crystalline magnesium silicate as defined in claim 1 wherein R is at least one of chromium, iron, aluminum, boron or a mixture thereof.

6. A porous crystalline magnesium silicate as defined in claim 3 or 5 wherein M is sodium or potassium.

7. A porous crystalline magnesium silicate as defined in claim 1 wherein M is hydrogen or a mixture of hydrogen and another ion.

8. A porous crystalline magnesium silicate as defined in claim 1 further characterized by infrared analysis having the pattern of FIG. 1 or FIG. 2 in the 1200-980 $cm^{-1}$ region.

9. A porous crystalline magnesium silicate as defined in claim 8 further characterized by infrared analysis in that said analysis exhibits at least one or more additional peaks at 1225±10 $cm^{-1}$, 800±20 $cm^{-1}$, 620±10 $cm^{-1}$, 550±20 $cm^{-1}$ and 450±20 $cm^{-1}$.

10. A porous crystalline magnesium silicate as defined in claim 8 wherein said distinct infrared analysis peaks are present both before and after calcination at about 500°- C. 700° C.

11. A porous crystalline magnesium silicate as defined in claim 10 wherein said silicate when subjected to differential thermal analysis in an air atmosphere using alumina as a reference and at a heating rate of about 20° C. per minute and with an air flow rate of about 50 cc per minute reveals a distinct exotherm at 870±30° C.

12. A porous crystalline magnesium silicate as defined in claim 11 further characterized by having at least those X-ray diffraction lines given in Table III of the specification both before and after said exotherm at 870±30° C.

13. A porous crystalline magnesium silicate as defined in claim 1 wherein said silicate when subjected to differential thermal analysis using alumina as a reference and a heating rate of about 20° C. per minute in an air atmosphere at an air flow rate of about 50 cc per minute reveals a distinct exotherm at 870±30° C.

14. A porous crystalline magnesium silicate as defined in claim 13 further characterized by having at least those X-ray diffraction lines given in Table III of the specification both before and after said exotherm at 870±30° C.

* * * * *